United States Patent [19]

Chen

[11] 3,941,133

[45] Mar. 2, 1976

[54] STOMAL DEVICES HAVING CONTROLLED RELEASE

[75] Inventor: James Ling Chen, East Brunswick, N.J.

[73] Assignee: E. R. Squibb & Sons, Inc., Princeton, N.J.

[22] Filed: Oct. 4, 1974

[21] Appl. No.: 512,278

[52] U.S. Cl. ............................... 128/283; 128/156
[51] Int. Cl.² ............................................. A61F 5/44
[58] Field of Search ......... 128/283, 296, 286, 156, 128/155; 156/219, 220, 221; 264/293

[56] References Cited
UNITED STATES PATENTS

| | | | |
|---|---|---|---|
| 3,053,252 | 9/1962 | Wolf | 128/296 X |
| 3,339,546 | 9/1967 | Chen | 128/156 |
| 3,457,919 | 7/1969 | Harbard | 128/156 |
| 3,522,807 | 8/1970 | Millenbach | 128/283 |
| 3,713,445 | 1/1973 | Marsan | 128/283 |
| 3,802,436 | 4/1974 | Brondberg | 128/283 |

*Primary Examiner*—John D. Yasko
*Attorney, Agent, or Firm*—Lawrence S. Levinson; Merle J. Smith; Stephen B. Davis

[57] ABSTRACT

Stomal devices having controlled release so that disposable stoma bags can be easily replaced without disturbing the peristomal covering attached to the skin. One such device comprises a peristomal covering including an adhesive member and backing member formed of polymeric material having a geometric pattern embossed therein. Another embodiment comprises attaching such embossed polymeric material directly to the adhesive face plate of a disposable stoma bag. Another embodiment comprises forming the stoma bag from the flexible embossed polymeric material which can serve as the backing member.

21 Claims, 6 Drawing Figures

STOMAL DEVICES HAVING CONTROLLED RELEASE

BACKGROUND OF THE INVENTION

Disposable stomal devices comprising an open-topped gusseted plastic bag (the open-top is sealed by an elastic band or belt when in use) having an adhesive face plate located near the sealed bottom or a completely sealed bag having such a face plate are in commercial use. The face plate is permanently bonded to the plastic bag and has an outer adhesive layer which attaches to the skin. The device is used by cutting a hole corresponding to the circumference of the stoma in the face plate and pressing the outer adhesive layer against the skin. The disadvantages of using such devices are the difficulty of removal of the filled bag from the skin and in fact for some bags solvent must be applied between the edge of the face plate and the skin to loosen the adhesive and the repeated removal of the bag affixed directly to the skin causes irritation and excoriation.

In order to overcome these problems, it has been proposed to employ the disposable bags described above in combination with peristomal coverings or bandages having a smooth thin polyethylene film backing. The bag is affixed directly to the film backing and the adhesive side of the peristomal covering is attached to the skin. Such coverings will permit removal of the stoma bag shortly after attachment, however, it is found that with time the adhesive bond between the bag face plate and film backing increases in strength to the extent that easy removal is no longer possible.

SUMMARY OF THE INVENTION

This invention is directed to an improvement over the disposable stomal devices described above. It is directed to a peristomal covering which will securely hold the weight of a filled plastic bag and yet permit the easy removal of the attached stoma bag. This result is achieved by the inclusion of a backing member on the peristomal covering as will be described below. Alternatively, the same result can be achieved by attaching the backing member directly to the adhesive face plate of the stoma bag or by forming the stoma bag from the flexible material which can serve as the backing member.

DETAILED DESCRIPTION

Figure 1:
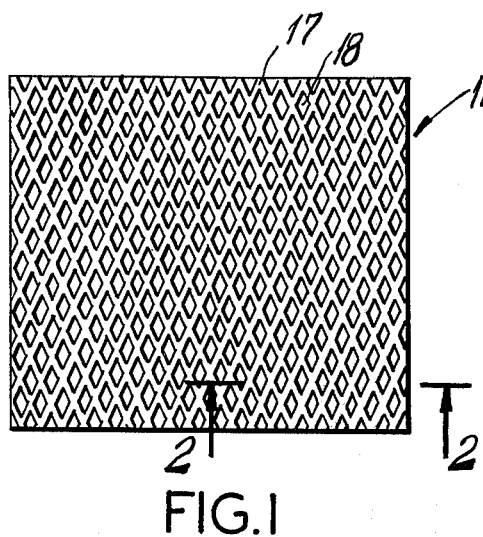
FIG. 1 is a top view of the peristomal covering of this invention.
Figure 2:
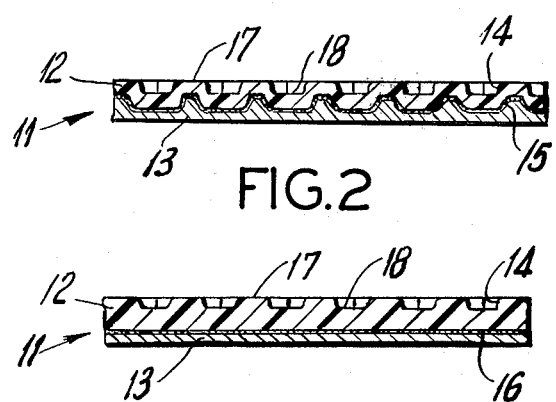
FIG. 2 is a side view taken along line 2—2 of the peristomal covering shown in FIG. 1.

Referring now to the drawings in more particular detail, the peristomal covering or bandage 11 includes backing member 12 and adhesive member 13 as best shown in FIG. 2. The peristomal covering 11 is preferably rectangular shaped as shown in FIG. 1 although other shapes such as circular can be used equally well and it can optionally include an inner circular hole to aid the user in increasing the hole size according to the circumference of the stoma.

The backing member 12 is preferably a sheet of flexible polymeric film such as polyethylene or polypropylene or a natural or synthetic rubber of from about 0.7 to about 5 mils thickness having a geometric pattern embossed therein. The embossed geometric pattern can include circles, rectangles, squares, triangles, diamonds, etc., with the diamond pattern shown in FIG. 1 being preferred. The embossed pattern results in the film having a side 14 with continuous raised ridges 17 separating each geometric dimple 18 as note FIGS. 1 and 2. The opposite side of the film, side 15, will of course have the geometric pattern raised.

Figure 3:
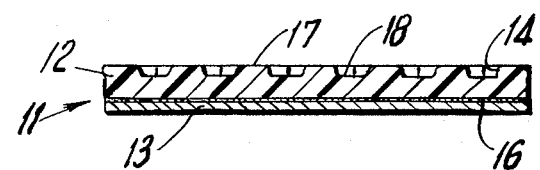
FIG. 3 is a side of a peristomal covering having a modified backing member.

Alternatively, the backing member 12 can be formed as a disc of rigid or semi-rigid polymeric material such as polyethylene or polypropylene or hard rubber or non-tacky natural or synthetic rubber materials having a thickness greater than about 2 mils, preferably more than 5 mils thick. The backing member 12 in this case can be formed by embossing or molding so as to have sides 14 and 15 as in FIG. 2 or a smooth bottom 16 as shown in FIG. 3.

The polymeric materials used as the backing member are normally transparent and colorless. However, these materials can be colored, for example to match the color of the skin. These materials, as well as methods of embossing and molding are known in the art and by themselves form no part of this invention.

The adhesive member 13 can be formed from any commercially available hygienically approved pressure sensitive adhesive material. Preferably, the adhesive member 13 comprises a pressure-sensitive rubbery elastomer adhesive component having intimately dispersed therein a water soluble or swellable hydrocolloid. A description of this type of bonding composition can be found in U.S. Pat. No. 3,339,546 whose disclosure is incorporated herein by reference. Various additives can also be included as a component of the adhesive member as for example antiinflammatory agents such as triamcinolene acetonide, antibiotics such as amphotericin B, anesthetics such as benzocaine and deodorants or agents which mask odor such as lemon oil.

When a backing member 12 having sides 14 and 15 as shown in FIG. 2 is employed, the adhesive member 13 should be of such thickness that the raised geometric pattern of side 15 will become embedded therein and not bond merely at the raised surface. The embedding is achieved by mechanically pressing, such as by calendaring, backing member 12 onto adhesive member 13 preferably while the adhesive member 13 is in a softened state. The force employed in calendaring the backing film 12 to the adhesive member 13 must be less than that which would flatten and destroy the embossing of backing film 12. When a backing member 12 having a smooth bottom as shown in FIG. 3 is employed, the thickness of the adhesive member is not critical and the bonding is again achieved by mechanical force.

A sheet of release agent coated paper is attached to the opposite side of adhesive member 13 during packaging of the peristomal covering 11. Silicone coated paper is preferred. This and other types of release agent coated paper are known in the art and are commercially available.

The peristomal covering 11 of this invention is used by cutting a hole or expanding the starting hole within the covering 11 according to the circumference of the stoma. A measuring device for this purpose can be packaged with the peristomal cover 11 in a hermetically sealed package. The release agent coated paper is then removed and discarded. The area around the stoma is cleaned and dried and the peristomal cover 11 is pressed firmly against the skin. Next the disposable stoma bag is attached by pressing the adhesive face plate firmly against exposed surface 14 of the backing member 12.

The peristomal cover 11 securely holds and supports the bag when filled and the backing member 12 also permits the bag to be easily peeled from the peristomal cover and be replaced by a fresh bag without removing the cover from the skin.

It is critical that the backing member 12 be attached to the adhesive member 13 so that side 14 having the continuous raised ridges 17 is exposed. It is by virtue of this orientation of backing member 12 that should there be leakage of fluid from the stoma bag, seepage across the backing member 12 to the edge of the covering 11 will be impeded by the continuous raised ridges 17. Otherwise, the seepage of such fluid would so weaken the bond between the bag and the covering 11 that a partially filled bag could not be supported.

Figure 4:
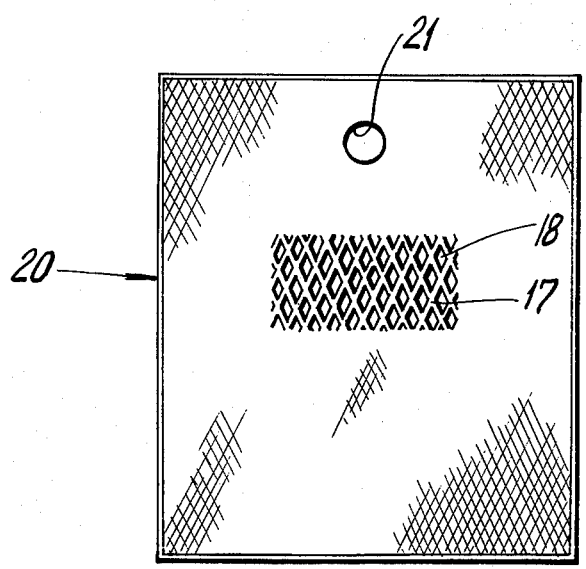
FIGS. 4 and 5 are front views of stomal devices according to alternate embodiments of this invention.

An alternate embodiment of this invention, shown in FIG. 4, comprises forming a disposable bag 20 directly from the embossed backing member 12 shown in FIG. 2. Such a bag can be formed from the sheet of polymeric film by conventional means such as by heat sealing or adhesive sealing the sheet into a tube and then sealing one or both ends of the tube. The bag 20 can include a circular starter hole 21 in the front wall so as to aid the user in increasing the hole size according to the circumference of the stoma. The bag 20 can be formed with gusseted sides. Methods and apparatus for forming the bag 20 from a sheet of flexible film are known in the art.

It is also within the scope of this embodiment to form the bag 20 from two sheets of flexible polymeric film. In this case, one sheet of embossed film, i.e. backing member 12 as shown in FIG. 2, is sealed to a sheet of smooth polymeric film so that the resulting bag 20 will have an embossed front wall and a smooth back wall. Also, it is possible to form the bag 20 so that only the area around the starter hole 21 (i.e. the area which will contact the adhesive member) is formed from the embossed film and the remainder of the bag is a smooth polymeric film.

The bag 20 is attached to the skin by means of an adhesive member not shown. This adhesive member is preferably a double sided pressure sensitive adhesive foam disc which is commercially available.

In this embodiment, it is critical that the side of bag 20 which is attached to the adhesive member have the continuous raised ridges 17 exposed. Again, it is by virtue of this orientation that seepage of fluid from the bag 20 is impeded and will not weaken the bond between the bag 20 and the adhesive member.

Figure 5:
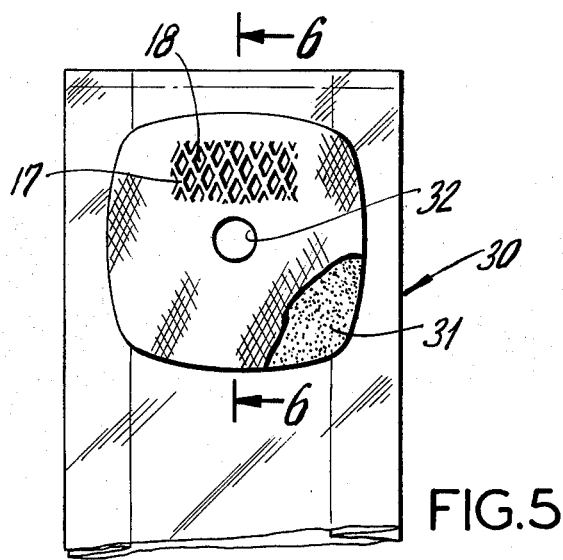
Figure 6:
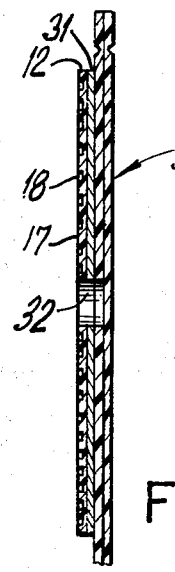
FIG. 6 is a side view of the alternate embodiment shown in FIG. 5 taken along line 6—6.

Another embodiment of this invention is shown in FIGS. 5 and 6. In this embodiment, a commercially available disposable plastic bag 30 having an adhesive face plate 31 is modified by attachment of the embossed backing member 12 shown in FIG. 2. FIG. 5 shows the bag 30 as having an open-top but the bag could also be sealed along all of its edges. A starter hole 32 can be included so as to aid the user in fitting the device to the stoma. The bag 30 is attached to the skin by means of an adhesive member, not shown, which is preferably the double sided pressure sensitive adhesive foam disc described above.

The bag 30 can be formed from any suitable flexible polymeric material such as polyethylene or polypropylene or a natural or synthetic rubber of a thickness of from about 0.7 to about 5 mils. The pressure sensitive adhesive face plate 31 is formed from any suitable bonding composition such as a combination of rubber, tackifiers, plasticizer and stabilizers.

Again, in this embodiment, it is critical that the backing member 12 be attached to the face plate 31 so that the side 14 having continuous raised ridges 17 is exposed. The bag 30 is attached to the skin by pressing exposed surface 14 against the double sided pressure sensitive adhesive foam disc. It is by virtue of this orientation that seepage of fluid from the bag 30 is impeded and will not weaken the bond between the bag 30 and the adhesive member.

What is claimed is:

1. A peristomal covering comprising an adhesive member attached to a polymeric backing member having an embossed geometric pattern wherein the exposed surface of said backing member has continuous raised uncoated ridges separating the geometric dimples said raised surface is adapted to be contacted by the adhesive face plate of a disposable stoma bag.

2. The peristomal covering of claim 1 wherein said polymeric backing member is a rigid or semi-rigid disc having a thickness greater than about 2 mils.

3. The peristomal covering of claim 2 wherein said polymeric backing member has a thickness greater than 5 mils and is formed from polyethylene, polypropylene, hard rubber, or non-tacky natural or synthetic rubber materials.

4. The peristomal covering of claim 1 wherein said polymeric backing member is a sheet of flexible film of from about 0.7 to about 5 mils thick.

5. The peristomal covering of claim 4 wherein said flexible film is polyethylene, polypropylene, or a natural or synthetic rubber.

6. The peristomal covering of claim 1 having a centrally located starter hole which can be expanded in order to fit around a stoma.

7. The peristomal covering of claim 1 wherein the embossed geometric pattern is diamond shaped.

8. The peristomal covering of claim 1 wherein the adhesive member comprises a pressure-sensitive rubbery elastomer adhesive having intimately dispersed therein a water soluble or swellable hydrocolloid.

9. A stomal device comprising a flexible polymeric bag having at least an area of one wall formed from a polymeric film of from about 0.7 to about 5 mils thickness and having an embossed geometric pattern wherein the exposed outer surface of said wall has continuous raised ridges separating the geometric dimples.

10. The stomal device of claim 9 wherein said bag is open-topped.

11. The stomal-device of claim 9 wherein said bag is sealed at all outer edges.

12. The stomal device of claim 9 wherein the entire bag is formed from the embossed polymeric film.

13. The stomal device of claim 9 wherein said bag has a starter hole and the embossed polymeric film is present only in the area of the starter hole and the remainder of the bag is formed from a smooth polymeric film of from about 0.7 to about 5 mils thickness.

14. The stomal device of claim 9 wherein said bag has one wall formed of the embossed polymeric film and the other wall is formed from a smooth polymeric film of from about 0.7 to about 5 mils thickness.

15. The stomal device of claim 9 wherein said embossed polymeric film is polyethylene, polypropylene, or a natural or synthetic rubber.

16. The stomal device of claim 9 wherein said embossed geometric pattern is diamond shaped.

17. A stomal device comprising a bag formed of flexible polymeric material having an adhesive face plate permanently bonded to an outer surface of said bag and a backing member of polymeric material having an embossed geometric pattern attached to said face plate wherein the exposed surface of said backing member has continuous raised ridges separating the geometric dimples.

18. The stomal device of claim 17 wherein said backing member is a sheet of flexible film of from about 0.7 to about 5 mils thickness.

19. The stomal device of claim 18 wherein the adhesive face plate and backing member both are disc shaped and both have a centrally located hole.

20. The stomal device of claim 18 wherein the embossed geometric pattern is diamond shaped.

21. The stomal device of claim 18 wherein said backing member is polyethylene, polypropylene, or a natural or synthetic rubber.

* * * * *